United States Patent [19]
Kawai et al.

[11] Patent Number: 5,871,352
[45] Date of Patent: Feb. 16, 1999

[54] APPARATUS FOR ANALYZING DISTRIBUTION OF CONTACT PRESSURE IN TEMPOROMANDIBULAR JOINT

[75] Inventors: Tadahiko Kawai; Norio Takeuchi, both of Tokyo; Etsuhide Yamamoto; Kiyomasa Nakagawa, both of Kanazawa, all of Japan

[73] Assignees: Tadahiko Kawai, Tokyo; Kiyomasa Nakagawa, Ishikawa-ken; Norio Takeuchi, Tokyo, all of Japan

[21] Appl. No.: 869,991

[22] Filed: Jun. 5, 1997

[30] Foreign Application Priority Data

Jun. 5, 1996 [JP] Japan ................................ 8-163603

[51] Int. Cl.$^6$ .................................................. A61C 19/05
[52] U.S. Cl. ............................................. 433/72; 600/590
[58] Field of Search .................................. 433/68, 69, 72; 600/589, 590

[56] References Cited

U.S. PATENT DOCUMENTS

| | | | |
|---|---|---|---|
| 4,528,627 | 7/1985 | Cohen | 433/69 |
| 5,458,487 | 10/1995 | Komatsu et al. | 433/71 |

FOREIGN PATENT DOCUMENTS

| | | |
|---|---|---|
| 64-11291 | 2/1989 | Japan . |
| 6277240 | 10/1994 | Japan . |

*Primary Examiner*—Ralph A. Lewis
*Attorney, Agent, or Firm*—Wenderoth, Lind & Ponack, L.L.P.

[57] ABSTRACT

The quantitatively and objectively present invention provides an apparatus for evaluating the contact pressure distribution in a temporomandibular joint. Specifically, the mandible and cranium are converted to two-dimensional rigid body element models by use of positional data of their contact line acquired from an image input device to compose a rigid body spring model, where only vertical springs resisting in vertical direction to the contact line are assumed in temporomandibular joint portion and vertical springs resisting in vertical direction as well as shear spring resisting in the direction parallel to the contact line are assumed in the teeth portion. An external force converted from an assumed elevation myodynamia is exerted on this model, and based on the theory of a rigid body spring model, stresses at each of the springs are calculated to represent contact pressures due to reaction forces against the external force mentioned above.

At the time when these contradictory stresses of the negative stresses at the vertical springs of temporomandibular joint portion and the stress at the shear spring of teeth portion are both decreased to approximately 0 during repetition of the calculation steps the stress at each vertical spring of the temporomandibular joint portion is calculated and displayed of its distribution.

1 Claim, 5 Drawing Sheets

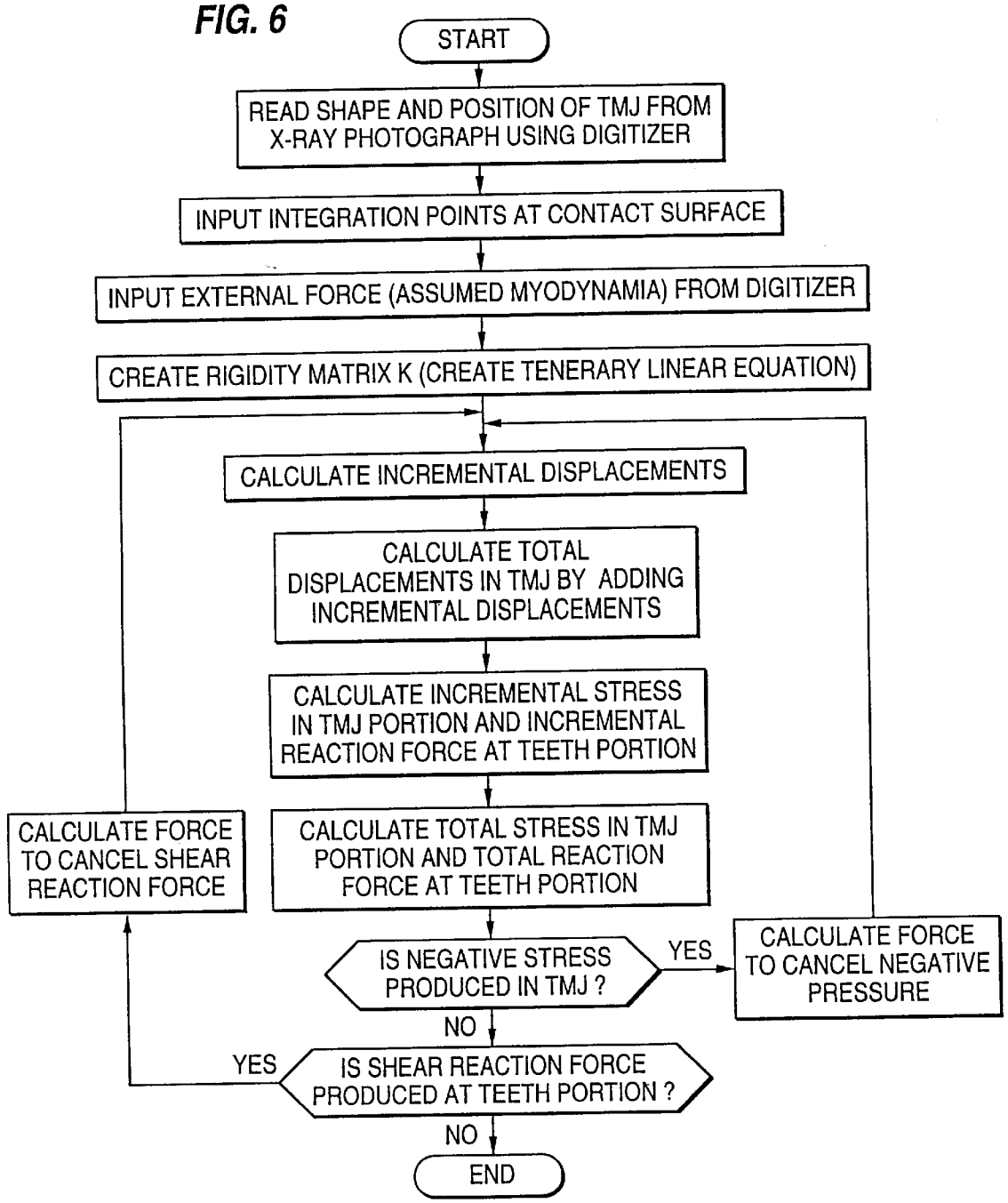

REFERNCE STATE

DISPLACED STATE

APPARATUS FOR ANALYZING DISTRIBUTION OF CONTACT PRESSURE IN TEMPOROMANDIBULAR JOINT

FIELD OF THE INVENTION

The present invention relates to an analyzer capable of quantitative and objective analysis of distribution of a contact pressure in temporomandibular joint.

DESCRIPTION OF PRIOR ART

One of major objects of surgical treatment of temporomandibular joint (to be called TMJ hereafter) disorders is to restore and maintain centripetal nature of TMJ which is said to be related to occlusion. Further, the same purpose can also be assumed on correcting abnormality in the position and form of the skeleton during treatment of jaw deformity. While various methods of treatment are being conducted, any of conventional methods of treatment is far from objective and quantitative, and is rather dependent on experience or intuition of doctors. As such, the effect of such treatment has not necessarily been satisfactory, and what has been done on this matter are mere academic discussions within the society for temporomandibular joint, the society for jaw deformities, etc.

For example, on a surgical treatment of a jaw deformity, sagittal split ramus osteotomy is carried out to incise ramus of the patient and to move the mandible to a proper position. In this case, a proper position of condyle (head of mandible) for retention of the mandible must be found.

It is anticipated that TMJ is under an unexperienced stress during such surgical treatment of jaw deformity because of the nature of the operation which is directed to an improvement of skeletal arrangement. It has been reported that if such a change of stress exceeds the tolerance of organism, destruction of TMJ progresses to cause osteoarthritis. Under such circumstances, there is a strong need to develop a method or apparatus for objectively and quantitatively evaluating and displaying a dynamic change of distribution of contact pressure in TMJ which may occur after surgery.

Referring to TMJ disorders, although they have been reported to be related to occlusion, no method or apparatus has been put to daily clinical use which facilitates objective and quantitative evaluation and display of actual dynamic characteristics of TMJ. Thus, there is a strong need for developing such an apparatus.

The above-described problems have also been encountered during treatments on a hip joint.

In the field of hip joint treatment, however, the above-described problems were solved by a diagnosing apparatus (Japanese examined patent publication (KOKOKU) No. S64-11291) invented by those including the inventors of the present invention. Specifically, this diagnosing apparatus is an application to a hip joint of a method of analyzing a non-linear problem for solid-dynamics by use of a rigid body spring model (Japanese examined patent publication (KOKOKU) No. S61-10771) invented by Tadahiko Kawai who is one of the inventors of the present invention. In this method, each portion of a hip joint is represented by elements of a rigid body spring model (to be called RBSM hereafter), respectively, and a load due to the weight of the patient is assumed as an external force exerted to the model, and a distribution of a stress at each point of contact can be correctly calculated only from a sectional X-ray photograph or the like, which helps improve the effect of treatments on hip joints.

Although it may be perfunctorily conceived to apply the above-mentioned diagnosing technique for hip joints according to Japanese examined patent publication (KOKOKU) No. S64-11291 as described above to studies on distribution of contact pressure in TMJ, no consideration to the effect of myodynamia is paid in this hip joint diagnosing technique (a detailed description on this issue will follow later). Therefore, this technique can not be applied to jaw joints where effect of myodynamia is the most important factor to consider, and thus the value of the myodynamia can not be obtained.

Since a mandible moves under the effect of myodynamia of masticatory muscles including a masseter muscle, etc., the effect of such myodynamia must be considered when studying distributions of contact pressure in TMJ. Presently, however, there is no way to identify the specific value of myodynamia and to know how it affects function of the mandible. This is the very reason why no objective and quantitative method has yet been developed to support dynamic analysis or surgical treatment concerned with jaw joints.

SUMMARY OF THE INVENTION

Taking the above-described situation into consideration, it is an object of the present invention to provide a diagnosing apparatus which makes it possible to evaluate the distribution of contact pressure in TMJ quantitatively and objectively, thereby allowing diagnoses for TMJ disorders, as well as jaw deformities, to be made independently of the experience or intuition of doctors.

The inventors of the present invention studied the possibility of evaluating distributions of contact pressure in TMJ in a different way from that disclosed in the above-mentioned Japanese examined patent publication No. S64-11291 for analyzing the distribution of contact pressure at a hip joint, although based on the above-described method of analysis utilizing RBSM (Japanese examined patent publication No. S61-10771).

A brief description will now be made on the dynamic method of analysis according to the theory of RBSM which is the basis of the present invention. Let us assume a RBSM which is generally comprised of, as shown in FIGS. 8A and 8B, two rigid triangular plate elements of unit thickness which are free from in-plane deformation due to stress 11 and 12 as well as two kinds of spring elements Kn and Ks which resist vertical forces and shear forces present in their contact surfaces (the boundary side AC or (3)-(5) in FIG. 8A), respectively. Then, displacement of an arbitrary point S on the triangular plates 11 and 12 as a result of deformation of the RBSM, in other words, relative displacement of the rigid triangular plates 11 and 12 in response to an external force P, is expressed by use of a displacement of reference points 1 and 2 of respective plates as a function of three components of translation (u and v) and rotation ($\theta$). Namely, Equation 1 shown below holds where a displacement of the arbitrary point S (S'→S") is represented by $[U_I V_I; U_{II} V_{II}]^t$ and a displacement of reference points 1 and 2 is represented by $[u_1\ v_1\ \theta_1;\ u_2\ v_2\ \theta_2]^t$. Here a centroid of each plate is usually adopted for the above reference point. Meanwhile, Equation 2 shown below can be derived where R represents a matrix for a coordinate transformation between a global coordinate system and a local coordinate system. And, a relative displacement vector $\overline{\delta^S}$ a of the point S by displacement (S'→S") is given by Equation 3 shown below. The symbols accompanied by a superscribed bar in those equations indicate components in a local coordinate system defined along the boundary side of the element (3)-(5) (this notation equally applies to the subsequent equations). The equations mentioned above may be summarized into Equation 4 shown below which expresses the relative displacement vector $\delta^S$ of the point S by displacement using a displacement vector $\mathbb{u}$ of the reference point.

Meanwhile, a relation between a stress $\sigma$ and a relative displacement $\delta^S$ are expressed by Equation 5 shown below. Spring constants can be obtained in the same way, but the description to calculate them is omitted. The primary object of the present invention is to evaluate the change of a distribution of contact pressure on vertical springs and not to obtain the absolute value of contact pressure on each spring, hence the spring constants may be of an arbitrary constant value at this time.

Based on the above relations, potential energy V accumulated in the springs distributed between two rigid body elements of the RBSM after deformation is given by Equation 6 shown below. Accordingly, by applying a theorem of a minimum potential energy as expressed by Equation 7 shown below, a rigidity matrix K for each spring element can be derived, the result of which is expressed by Equation 8 shown below.

Since $P_{x1}$, $P_{y1}$, $M_1$, $P_{x2}$, $P_{y2}$, $M_2$ respectively represent components of an external force P in X-direction, Y-direction, and angular direction $\theta$ (corresponding to moments M1 and M2), the displacement $u_i$, $v_i$ and $\theta_i$ (i=1,2) can be calculated if the external force P is known. Substituting this displacement into Equation 4, the relative displacement vector $\delta^S$ can be calculated, and, from this $\delta^S$ and Equation 5, the stress $\hat{\sigma}$ is finally obtained.

Note that in the foregoing as well as succeeding explanations, the term stress distribution is sometimes used to imply a contact pressure distribution in the sense that stress will yield at a spring under contact pressure and hence distribution patterns of the two are similar in cases where the spring constant is fixed.

$$\mathbb{U} = \mathbb{Q} \cdot \mathbb{u}_i \quad \text{(Equation 1)}$$

where $$\mathbb{U} = \lfloor \mathbb{u}_I {}^v{}_I;\ \mathbb{u}_{II} {}^v{}_{II} \rfloor^t$$

$$\mathbb{Q} = \begin{pmatrix} 1 & 0 & -(y-y_{G1}) & & & \\ 0 & 1 & (x-x_{G1}) & & 0 & \\ \hline & & & 1 & 0 & -(y-y_{G2}) \\ & 0 & & 0 & 1 & (x-x_{G2}) \end{pmatrix}$$

$$\mathbb{u}_i = \lfloor u_1 v_1 \theta_1;\ u_2 v_2 \theta_2 \rfloor^t$$

$$\mathbb{U} = R \cdot \mathbb{U} \quad \text{(Equation 2)}$$

where $$R = \begin{pmatrix} l_1 m_1 & & & \\ l_2 m_2 & & 0 & \\ \hline & & l_1 m_1 & \\ & 0 & l_2 m_2 & \end{pmatrix} \quad \begin{array}{l} l_1 = \cos(\bar{x}, x) = y_{35}/l_{35} \\ l_2 = \cos(\bar{x}, y) = x_{35}/l_{35} \\ m_1 = \cos(\bar{y}, x) = x_{35}/l_{35} \\ m_2 = \cos(\bar{y}, y) = y_{35}/l_{35} \end{array}$$

$$\delta = M \cdot \mathbb{U} \quad \text{(Equation 3)}$$

$$\left\{ \begin{array}{c} \overrightarrow{(P'P'')_x} \\ \overrightarrow{(P'P'')_y} \end{array} \right\} = \left\{ \begin{array}{c} \delta_n \\ \delta_s \end{array} \right\} = \begin{pmatrix} -1 & 0 & 1 & 0 \\ 0 & -1 & 0 & 1 \end{pmatrix} \left\{ \begin{array}{c} \bar{U}_I \\ \bar{V}_I \\ \bar{U}_{II} \\ \bar{V}_{II} \end{array} \right\}$$

$$\delta = M \cdot R \cdot \mathbb{Q} \cdot \mathbb{u}_i = B \cdot \mathbb{u}_i \quad (B = M \cdot R \cdot \mathbb{Q}) \quad \text{(Equation 4)}$$

$$B = \begin{pmatrix} -l_1 & -m_1 & l_1(y-y_{G1}) - m_1(x-x_{G1}) & & & \\ -l_2 & -m_2 & l_2(y-y_{G1}) - m_2(x-x_{G1}) & & & \\ \hline & & & l_1 & m_1 & -l_1(y-y_{G2}) + m_1(x-x_{G2}) \\ & & & l_2 & m_2 & -l_2(y-y_{G2}) + m_2(x-x_{G2}) \end{pmatrix}$$

$$\sigma = D \cdot \delta \quad \text{Equation 5)}$$

$$\sigma = \lfloor \sigma_n \sigma_s \rfloor^t \quad \text{(Stress)} \quad \text{(Equation 6)}$$

$$\delta = \lfloor \delta_n \delta_s \rfloor^t \quad \text{(Relative displacement)}$$

$$D = \begin{pmatrix} k_n & 0 \\ 0 & k_s \end{pmatrix} \quad \text{(Spring matrix)}$$

$$= \frac{1}{2} \int_{l_{35}} \delta^t D\, \delta ds$$

$$= \frac{1}{2}\ \mathbb{u}_i{}^t \int_{l_{35}} (B^t D B) ds\ \mathbb{u}_i$$

$$\frac{\partial V}{\partial \mathbb{u}_i} = K\, \mathbb{u}_i \quad \text{(Equation 7)}$$

$$\text{(Equation 8)}$$

$$\left\{ \begin{array}{c} P_{x1} \\ P_{y1} \\ M_1 \\ \hline P_{x2} \\ P_{y2} \\ M_2 \end{array} \right\} = \begin{pmatrix} K_{11} & K_{12} & K_{13} & K_{14} & K_{15} & K_{16} \\ & K_{22} & K_{23} & K_{24} & K_{25} & K_{26} \\ & & K_{33} & K_{34} & K_{35} & K_{36} \\ \hline & & & K_{44} & K_{45} & K_{46} \\ & \text{SYM} & & & K_{55} & K_{56} \\ & & & & & K_{66} \end{pmatrix} \left\{ \begin{array}{c} u_1 \\ v_1 \\ \theta_1 \\ \hline u_2 \\ v_2 \\ \theta_2 \end{array} \right\}$$

-continued where $$\begin{cases} K_{11} = k_n y^2{}_{35} + k_s x^2{}_{35} \\ K_{12} = -(k_n - k_s) y_{35} x_{35} \\ K_{13} = k_n y_{35} \Delta_{11} - k_s x_{35} \Delta_{21} \\ K_{14} = K_{11} \\ K_{15} = K_{12} \\ K_{16} = k_n y_{35} \Delta_{22} - k_s x_{35} \Delta_{12} \end{cases} \quad \begin{cases} K_{22} = k_n x^2{}_{35} + k_s y^2{}_{35} \\ K_{23} = -(k_n x_{35} \Delta_{11} + k_s y_{35} \Delta_{21}) \\ K_{24} = -K_{12} \\ K_{25} = -K_{22} \\ K_{26} = -(k_n x_{35} \Delta_{22} + k_s y_{35} \Delta_{12}) \end{cases}$$

$$\begin{cases} K_{33} = k_n \Delta^2{}_{11} + k_s \Delta_{21} + \dfrac{k_n}{12} l^4_{35} \\ K_{34} = -K_{13} \\ K_{35} = -K_{23} \\ K_{36} = k_n \Delta_{11} \Delta_{22} + k_s \Delta_{21} \Delta_{12} - \dfrac{k_n}{12} l^4_{35} \end{cases} \quad \begin{cases} K_{44} = K_{11} \\ K_{45} = K_{12} \\ K_{46} = -K_{16} \end{cases}$$

$$\begin{cases} K_{55} = K_{22} \\ K_{56} = -K_{26} \end{cases} \left( K_{66} = k_n \Delta^2{}_{22} + k_s \Delta^2{}_{12} = \dfrac{k_n}{12} l^4_{35} \right)$$

and $K_u \sim K_{66}$ are multiplied by $$\begin{cases} 2\Delta_{11} = x_{35}(x_{31} + x_{51}) + y_{35}(y_{31} + y_{51}) \\ 2\Delta_{12} = x_{35}(y_{32} + y_{52}) - y_{35}(x_{32} + x_{52}) \\ 2\Delta_{21} = -x_{35}(y_{31} + y_{51}) + y_{35}(x_{31} + x_{51}) \\ 2\Delta_{22} = -x_{35}(x_{32} + x_{52}) - y_{35}(y_{32} + y_{52}) \end{cases}$$

where $(x_{ij}=x_i-x_j, Y_{ij}=y_i-y_j)$

While a description has been made on a method of analysis based on the theory of RBSM applied for the case of two rigid triangular plates and two kinds of springs Kn and Ks provided there between, a description will now be made on the difference encountered when the method is applied to a jaw joint which is the object of the present invention.

A mandible 3 and a cranium 4 shown in FIG. 2 are replaced by plane element models of rigid bodies 3A and 4A having unit thickness and being free from in-plane deformation by stress as shown in FIGS. 3 through 5, mainly focusing on TMJ portion 1 and the teeth portion 2.

Contact pressure as the surface force in the vertical direction (normal to the surface) acts over the regions along their contact line between the mandible 3 and the cranium 4 in the TMJ portion 1, in other words between the rigid bodies 3A and 4A.

Integral points of group B are provided as reference points for calculating contact pressure along the contour line of the rigid body 3A as shown in FIG. 3, and the springs Kn which resist in the vertical direction are also set at these integral points as shown in FIG. 4. The integral points of group B are provided only in a region where rigid bodies 3A and 4A (or the head of the mandible 3 and the cranium 4) contact each other. Also, it is assumed, that their surfaces of contact in the TMJ portion 1 is relatively smooth so as not to resist in a shear direction which is tangential to the surface.

Next, as shown in FIG. 3, a integral point of C is also provided at a certain position along the contact line of dentition with the cranium 4 in the teeth portion 2. Vertical spring Kn is provided because a reaction force acts in the vertical direction against the dentition in this portion. At the same time, shear spring Ks acting in a shear direction is also assumed. This shear spring Ks is assumed to correspond to a virtual frictional force as a transient dummy to be absorbed into myodynamia, of which value is gradually corrected and converged to a most appropriate value from its initial uncertainty through repetitive calculations.

As shown in FIG. 3, the reference point for displacement of the rigid body 3A is positioned at the corner of mandibular angle (gonial angle) E. This is the point where an external force due to a masseter muscle and a medial pterygoid muscle which are primarily contributing to elevate the mandible 3 is to be exerted, and three degrees of freedom of displacement, namely translation (u, v) and rotation (θ), are given to the rigid body 3A as regards this reference point. All the myodynamia referred to above are converted and integrated to compose a single external force acting on this point E.

On the other hand the displacement of the rigid body 4A is set to 0; i.e., treated as a fixed element. The reason of this treatment is that deformation of the RBSM as a whole can be regarded as a relative displacement of the one rigid body element to the other, and that calculations in the following will greatly be simplified by fixing one of the rigid body elements.

Since it has been assumed, in elements of the RBSM so far explained, that the rigid body 4A is fixed and that there is no resistance in the shear direction in TMJ portion 1, the above-mentioned Equations 4 through 8 concerning the relative displacement vector $\delta$ will be developed into Equations 9 through 12 as shown below for each of TMJ portion 1 and teeth portion 2 in FIG. 3. In the equations shown below, B represents a transformation matrix, u represents a displacement vector of rigid body, and V represents potential energy accumulated in all springs.

TMJ PORTION)

$$\delta = B \cdot u \qquad \text{(Equation 9)}$$

where $(u)=(u, v, \theta)$ $B=[l_1 \; m_1 -l_1(y-y_G)+m_1(x-x_G)]$ $V=\tfrac{1}{2}\!\int(\delta^t\!\cdot\!D + ee \cdot fheight\,\delta)ds = +e, fra\; 1/2 \; u \; f(\,Bt\!\cdot\!D\!\cdot\!\overline{B})d\!$ (Equation 10)

where $(\delta = \delta_n), \overline{D}=[k_n]$ (TEETH PORTION)

$$\delta = B \cdot u \qquad \text{(Equation 11)}$$

where $u =(u, v, \theta)$ $$B = \begin{pmatrix} l_1 m_1 - l_1(y - y_G) + m_1(x - x_G) \\ l_2 m_2 - k_2(y - y_G) + m_2(x - x_G) \end{pmatrix}$$

$V=\tfrac{1}{2}\!\int(\delta^t\!\cdot\!D\!\cdot\!\delta)ds = \tfrac{1}{2}\; u\; f(\,B^t\!\cdot\!D\!\cdot\!B)ds\cdot u$ (Equation 12)

where $$D = \begin{pmatrix} k_n & 0 \\ 0 & k_s \end{pmatrix}$$

A rigidity matrix K for each spring element is derived by applying the above-mentioned theorem of minimum potential energy (Equation 7) to each of Equations 10 and 12, in the form of a modified Equation 8. By superposing such rigidity matrices for all of the spring elements provided at integral points of group B or C shown in FIG. 3, tenerary linear equations including variables u, v and θ can be obtained.

Since the value of an overall rigidity matrix K, obtained by the superposition as mentioned above, equals the external force P caused by the aforementioned myodynamia, variables u, v and θ can be obtained by solving this equation. Successively, relative displacement $\bar{\sigma}^F$ or $\bar{\sigma}^F$ accompanied by a superscribed bar at each of the abovementioned integral points can be obtained by use of Equations (9) and (11) as regards group of integral points B or C, in other words, the TMJ portion 1 or the teeth portion 2 of mandible. Then the stress σ in each of vertical as well as shear springs Kn and Ks are obtained from Equation (5).

A description will now be made on the method of obtaining the external force P, which is the specific feature of the method of analysis in the present invention as applied to jaw joints.

According to the method of analyzing the distribution of contact pressure at a hip joint disclosed in Japanese examined patent publication No. S64-11291, since the weight of the patient which is already known is adopted as an external force P to act on the femoral head via the acetabulum, a relative displacement of the femoral head can be readily calculated. Thus, the stress at each spring can be calculated using Equation 5 to obtain a distribution of contact pressure in the hip joint.

To the contrary, an external force applied to the jaw joint in the present invention is myodynamia produced by masticatory muscles which can not be measured. Hence, external force P needed to derive relative displacement σ can not be determined beforehand. This means that the method for analyzing the hip joint according to Japanese examined patent publication No. S64-11291 can not be applied for a jaw joint as it is.

From simple consideration of an organic system taken from a view point of balancing forces on a mandible of jaw joint, the forces that react against the myodynamia elevating mandible 3 shown in FIG. 2 include not only a reaction force at the TMJ portion 1 but also a reaction force in the teeth portion 2, because the masseter muscle, which greatly contributes to elevation, strongly acts at the molarae portion.

Since the reaction force in the teeth portion 2 seems to act in the vertical direction relative to the dentition only, it is contemplated that if any frictional reaction force is generated as a result of calculation based on a RBSM theory and using an assumed value of myodynamia as input external force, this reaction force is contradictory to the actual reaction force in the teeth portion 2.

In this case, the contradictory reaction force may well be corrected by changing the myodynamia. Namely, in the calculation based on the RBSM theory, a force to counteract and cancel the contradictory reaction force is to be added in order to introduce a change of myodynamia. Then a recalculation is carried out using the corrected value of the myodynamia as a new external force P, and this calculation loop will be repeated until the stress at every integral point of the TMJ portion 1 and the reaction force in the teeth portion 2 converges to a tolerable value (as to be explained later), and thus the distribution of contact pressure in the joint portion 1 will be obtained eventually.

An apparatus for analyzing distribution of contact pressure in TMJ according to the present invention has been devised based on the background concept as described above, i.e., a quite novel idea that the magnitude of external force, (or myodynamia) which was initially unknown, is gradually converged into a proper value through repeated calculations, while the distribution of contact pressure is obtained simultaneously. Namely, the apparatus is characterized in that it has a feature as described below.

There is provided an apparatus for analyzing the distribution of contact pressure in TMJ comprising:

a means for acquiring positional data of a contact line between a mandible 3 and a cranium 4 from a sectional image taken in the side vertical plane extending in the axial direction of the cranium 4 and including the contact line;

a calculation means for performing all of following (A) to (D):

a calculation step (A) wherein rigid body element models having unit thickness in a direction perpendicular to the side vertical plane and free from in-plane deformation by stress are substituted for the mandible 3 and the cranium 4 based on shapes obtained from the positional data of the contact line; regions of the element models along the contact line of the mandible 3 and the cranium 4 are divided into a finite number of plane elements having a unit depth; only vertical springs Kn resisting in a direction vertical to the contact line are assumed for the plane elements in the TMJ portion 1 among the divided plane elements; a shear spring Ks resisting in a tangential direction and a vertical spring Kn resisting in a direction vertical to the contact line are assumed for the plane elements in the teeth portion 2; it is so conditioned that a displacement of the plane elements of the mandible 3 is confined into two-dimensional directions within the side vertical plane; thus, stresses $\sigma_n$, $\sigma_s$, and $\sigma_n$ are produced at the vertical spring Kn in the TMJ portion 1, the shear spring Ks in the teeth portion 2 and the vertical spring Kn in the teeth portion 2 are calculated from the positional data of each plane element, using assumed value of myodynamia as an external force P with an assumption that a reaction force from the cranium 4 against the myodynamia is exerted on the mandible 3 in the TMJ portion 1 and on a position in the teeth portion 2;

a calculation step (B) wherein it is examined whether a negative stress is produced or not at the vertical springs Kn in the TMJ portion 1 and, if a negative stress is present, a constraint canceling the negative stress is calculated, a force having the same magnitude as and opposite sign to the constraint is added to the myodynamia, and the calculation of stress in the calculation step (A) is repeated using the corrected myodynamia as the corrected external force P;

a calculation step (C) wherein it is examined whether a stress is produced or not at the shear spring Ks in the teeth portion 2 and, if a stress is present, a force canceling the stress is calculated and the calculation of stress in the calculation step (A) is repeated using corrected myodynamia obtained by adding the canceling force to the myodynamia as the corrected external force P; and a calculation step (D) wherein during the repetition of the calculation steps (B) and (C), stress $\sigma_n$ at each of the vertical springs Kn in the TMJ portion 1 is calculated at the moment when the negative stress at the vertical springs Kn in TMJ portion 1 and the stress at the shear spring Ks in the teeth portion 2 are both decreased to 0 or a negligible level; and a display means for displaying the distribution of the stress at the vertical springs along the contact line in the TMJ portion 1 based on the result of the calculations.

Preferably, input of the assumed myodynamia value as an external force P for the first time at the calculation step (A) is an empirically estimated value to make repeated calculations converge more efficiently.

BRIEF DESCRIPTION OF THE DRAWINGS

FIG. 6 is a flow chart showing an operation procedure of analysis based on an embodiment of the present invention.

DETAILED DESCRIPTION OF PREFERRED EMBODIMENT

A preferred embodiment of the present invention will now be described with reference to the drawings.

Figure 1:
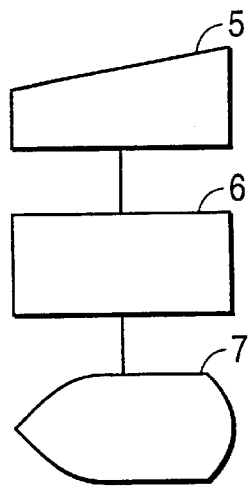
FIG. 1 is a block diagram showing a configuration of an analyzer according to an embodiment of the present invention.
Figure 2:
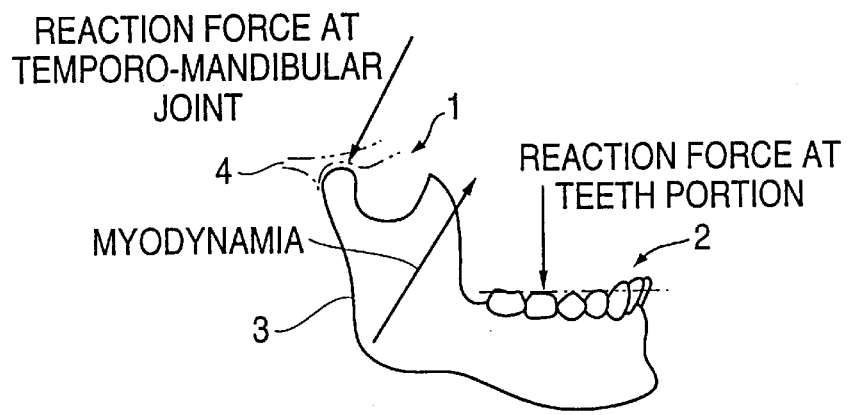
FIG. 2 illustrates an organic system with balancing forces around a jaw joint.

The simplest apparatus configuration of the present embodiment comprises a digitizer 5, a computer 6, and a graphic display 7 as shown in FIG. 1. The computer 6 is loaded with such software as executing data input, analysis calculations, and outputs and displays the relevant data. Although the following description proceeds based on such a configuration, it is needless to-say that the present invention is not limited to such a configuration. For example, a printer may be connected to the computer 6, and a scanner may be used instead of the digitizer 5.

Procedures for obtaining stress at each of vertical springs Kn at the integral points B in the TMJ portion 1 shown in FIG. 3 will be explained based on FIGS. 2 through 6. The flow chart in FIG. 6 shows the overall operation procedures. The sectional shape and position data of the jaw joint shown in FIG. 3, i.e., x- and y-coordinates of major points on the contour of plane element 3A, are input to the computer 6 from an X-ray photograph (sectional image) of the jaw joint using the digitizer 5.

Figure 3:
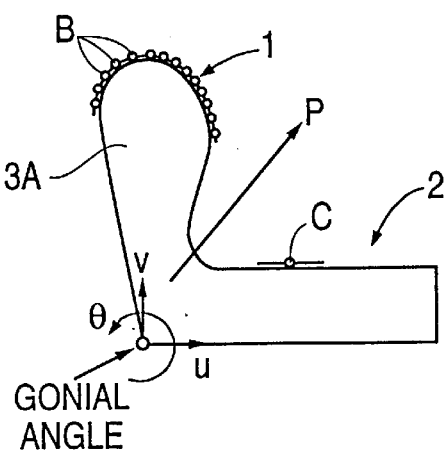
FIG. 3 is a sectional view of an element model as a replacement of the mandible in FIG. 2.

Next, the integral points of group B and C in FIG. 3 are defined along the contact line between the mandible 3 and the cranium 4 on the sectional image described above, and are inputted together with an assumed value of the myodynamia as an external force P using the digitizer 5. An empirical value estimated in advance is used as the value of the assumed myodynamia to cause subsequent repeated calculations to converge quickly.

Figure 4:
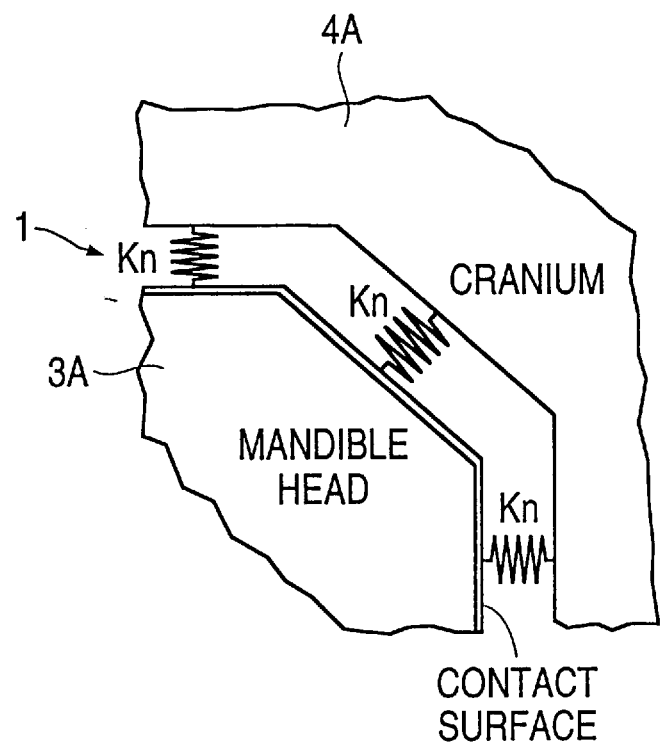
FIG. 4 is a partial sectional view showing element models in TMJ.
Figure 5:
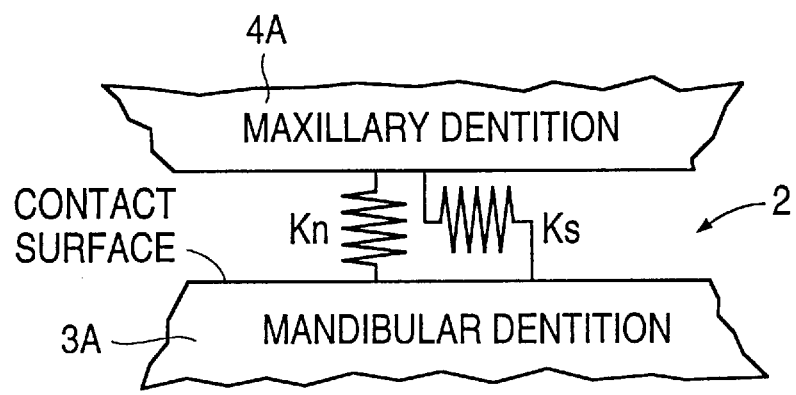
FIG. 5 is a partial sectional view showing element models in the teeth portion.

In the computer 6, element models comprised of rigid bodies 3A and 4A which are both free from in-plane deformation by stress, as shown in FIGS. 3 through 5, are composed based on the positional data of the contact line inputted from the digitizer 5, and substituted for the mandible 3 and the cranium 4 in the TMJ 1.

Note that figures of these rigid bodies 3A and 4A express the sectional view of the mandible 3 and the cranium 4 within a side vertical plane which includes a longitudinal (vertical) axis of the cranium 4, as well as that these rigid bodies have a unit thickness in the direction perpendicular to the plane.

Also it is assumed that a displacement of the plane element 3A of the mandible 3 is confined into two dimensional directions within the side vertical plane, while the plane element 4A of the cranium 4 is fixed.

Regions of those element models along the contact line of the mandible 3 and the cranium 4 are divided into a finite number of plane elements having unit depths into the direction perpendicular to the side vertical plane. These plane elements are so defined as to have the abovementioned integral points of groups B and C at their centers, respectively.

Only vertical springs Kn resisting in a direction perpendicular to the contact line are assumed for the plane elements in the TMJ portion 1 among the divided plane elements, and a shear spring Ks resisting in a tangential direction and vertical spring Kn resisting in a direction vertical to the contact line are assumed for plane elements in the teeth portion 2.

A rigidity matrix K or each spring element is derived by applying Equation 7 to each of Equations 10 and 12 in the form of modified Equation 8. By superposing such rigidity matrices for all of the spring elements provided at integral points of group B or C shown in FIG. 3, tenerary linear equations including variables u, v and θ can be obtained.

By solving the above tenerary linear equations, variables $u_1$, $v_1$ and $\theta_1$ can be obtained corresponding to the external force P caused by the assumed myodynamia. Successively, a relative displacement $\bar{\delta^s}$ or $\bar{\delta^s}$ accompanied by a superscribed bar at each of the above-mentioned integral points can be obtained by the use of Equations (9) and (11).

Finally, from Equation (5) the stress $\bar{\delta^s}$ ($\sigma_n$ and $\sigma_s$) in each of the vertical as well as the shearing springs Kn and Ks is obtained in the TMJ portion 1 and in the teeth portion 2. The increment of displacement in FIG. 6 is set at 0 at the first cycle of calculation.

Next, it is examined whether stress $\sigma_n$ produced is negative or not at any of the vertical springs Kn in the TMJ portion 1 based on the result of the calculation and, if a negative stress is found (determined YES), a constraint for temporarily canceling the negative stress is calculated and added to keep a balanced state, because such a negative stress (contact pressure) works for dislocating the TMJ which seems to be contradictory to the actual situations.

Further, as the above-mentioned constraint does not actually exist too, a force having the same magnitude as and opposite sign to the constraint is added to the present external force P, and a recalculation of the total displacement is executed. Practically, the increment of displacement (displacement has been set at 0 at the first cycle of calculation) is calculated corresponding to the additional force mentioned above. Then the increment of stress at each spring corresponding to this increment of displacement is calculated and is added to the previous stress value (which has been set at 0 at the first cycle of calculation) to obtain the total stress at each spring again. This loop of calculation is repeated until the negative stress reaches 0 or a negligible level.

When the negative contact pressure (stress) in the TMJ portion 1 thus converges to 0 or a value of a negligible level, then a stress $\sigma_s$ at the shear spring Ks in the teeth portion 2 is examined and, if a stress is present (determined YES), a force canceling the same is calculated and added to the initial external force P because such a stress is contradictory to actual situations. Then, the process returns to the calculation loop similar to that for correcting a negative stress as described above to recalculate the total displacement. This loop of calculation is repeated until the conflicting shear stress is decreased to 0 or a negligible level. Note that through calculations in the teeth portion 2 so far explained, a stress i is regarded as the same as the force because only one spring is being provided in this portion.

When both the negative stress at the vertical springs Kn in the TMJ portion 1 and the stress at the shear springs Ks in the teeth portion 2 are decreased to 0 or a negligible level (determined NO) after the repetition of the above-described loop of calculation, the stress $\sigma_n$ at each of the vertical springs in the TMJ portion 1 is calculated to terminate the calculation.

The negligible level mentioned in the foregoing explanations means a level of the order of $10^{-6}$ compared with the initially calculated stress value at the vertical springs Kn or the shear springs Ks, respectively.

Although the calculation should be repeated until such stresses become exactly 0 because they should never exist in the TMJ portion 1 and in the teeth portion 2, the final result obtained will not be adversely affected if these stresses are reduced to values within the calculation tolerance. As a guideline for this tolerance, a multiplication factor of the order of $10^{-4}$ at most, or $10^{-6}$ in general seems to be necessary.

The distribution of stress $\sigma$(contact pressure) at each of the vertical springs Kn in the TMJ portion 1 obtained upon termination of the above-described calculation procedures is displayed on the graphic display 7 shown in FIG. 1. A spring constant of 1, for example, may be assigned to each spring on calculating the stress for convenience.

The above-described embodiment of the present invention makes it possible to obtain and display an accurate distribution of stress. In other words, the contact pressure in the TMJ portion 1 can be obtained and displayed from an X-ray photograph of the jaw joint even if the myodynamia of masticatory muscles is unknown. By applying such an analytical process for various preoperative plans to treat malformation of jaw joint and comparing the results to each other, for instance, an ideal form and location of the jaw joint will be decided which is to be restored through the surgical operation from a viewpoint of the optimum distribution of contact pressure in the TMJ. This makes it possible to dramatically improve the effect of surgical treatment of the jaw joint.

Figure 7A:
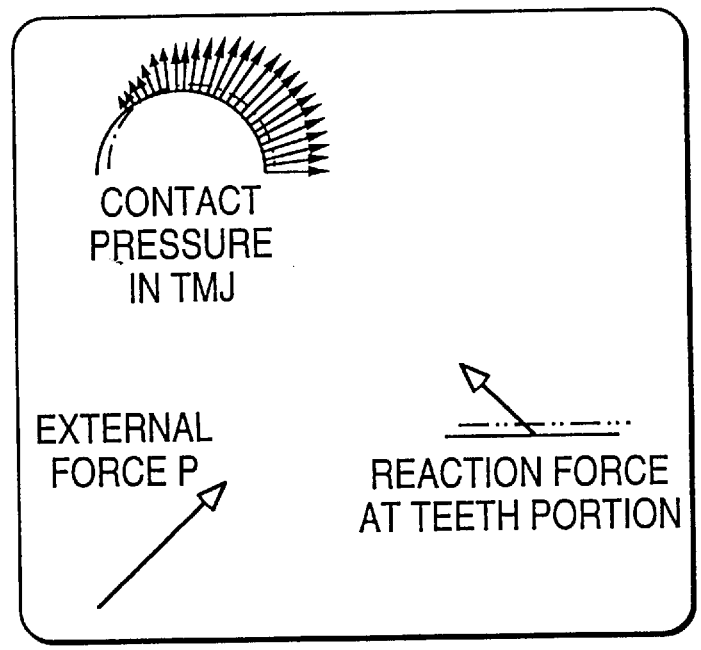
FIG. 7A is an illustration of initial calculation results according to the embodiment showing contact pressure in the TMJ portion, assumed external force P, and a reaction force in the teeth portion.

FIG. 7A illustrates the result of analysis at the first cycle of calculation including the contact pressures (i.e., stresses at the vertical springs Kn) in the TMJ portion 1, a reaction force (vector sum of the force produced at the vertical spring Kn and that produced at the shear spring Ks) in the teeth portion 2, and the external force (assumed myodynamia) P, in the above-described embodiment. The arrows represent vectors, and the double-dotted lines show the location of contour lines of the mandible head as well as dentition in the teeth portion after relative displacement.

Figure 7B:
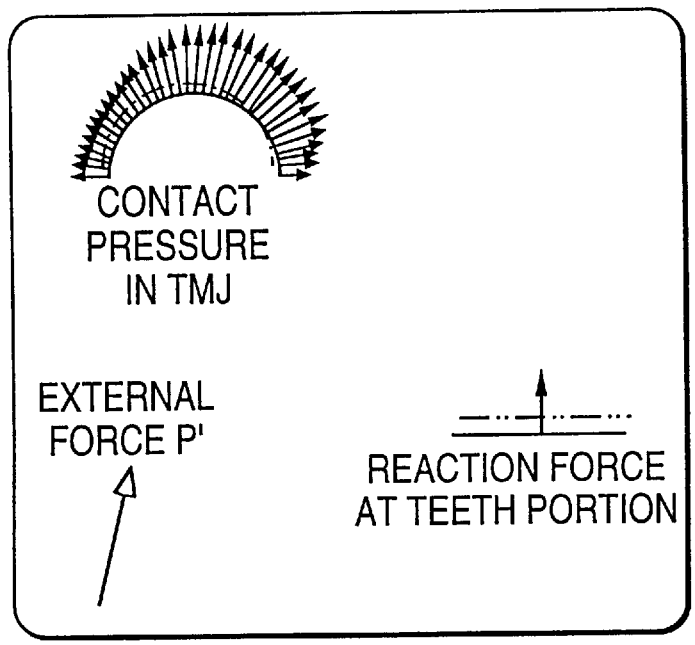
FIG. 7B is an illustration of final calculation results according to the embodiment showing contact pressure in the TMJ portion, final external force and a reaction force in the teeth portion obtained as converged after repeated calculations.
Figure 8A:
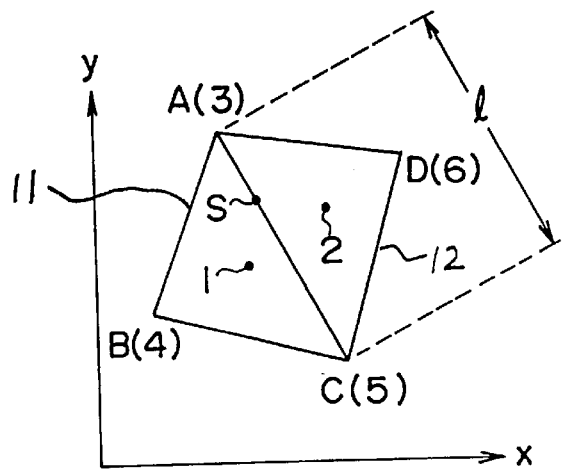
FIG. 8A is a conceptual plan of fundamental RBSM in a reference state comprised of two rigid triangular element models 11 and 12 as well as springs interposed between them.
Figure 8B:
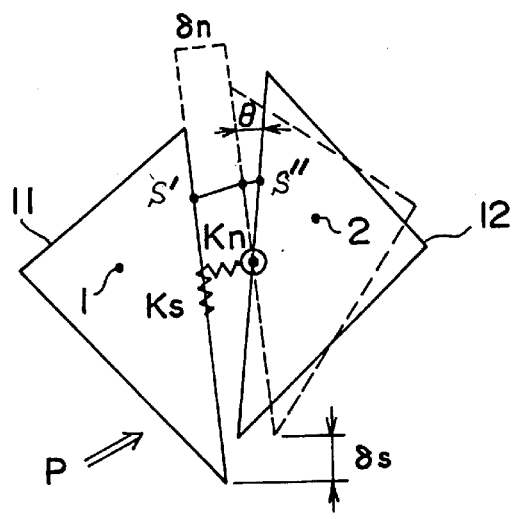
FIG. 8B is the same plan as FIG. 8A, wherein a deformed state (after relative displacement of the element models 11 and 12) of RBSM is shown.

It is apparent from these illustrations that a shear reaction force is present which does not actually appear in the teeth portion 2 because of the assumed myodynamia. Meanwhile, FIG. 7B illustrates the result obtained when both of the contact pressures in the TMJ and the reaction force in the teeth portion have converged through calculation loops shown in FIG. 6. As shown, the reaction force in the teeth portion is pointing almost upward as a result of the unnatural shear stress being canceled.

Correspondingly, the direction of external force (myodynamia) P' is also closer to the straight upward direction than at the first cycle of calculation (FIG. 7A), indicating that the direction of myodynamia has been corrected by the converging calculation. As a result, the distribution of the contact pressure in the TMJ portion 1 has spread more widely throughout the TMJ than that of the first cycle. Thus, as for the case of FIG. 7B, the TMJ can be regarded as in a stable state.

As has been explained in the foregoing paragraphs, an apparatus for analyzing the distribution of the contact pressure in the TMJ according to the present invention makes it possible to obtain and evaluate the distribution of the contact pressure in the TMJ quantitatively and objectively, and produces a quite significant effect in that an appropriate diagnosis or preoperative planning for a temporomandibular joint disorder or a jaw deformity can be realized without relying upon the experience or intuition of a doctor.

The foregoing description of the preferred embodiment of the invention has been presented for purposes of illustration and description. It is not intended to be exhaustive or to limit the invention to the precise form disclosed. Many modifications and variations are possible in light of the above teaching. It is intended that the scope of the invention be defined by the appended claims.

What is claimed is:

1. An apparatus for analyzing a distribution of a contact pressure in a temporomandibular joint, said apparatus comprising:

a means for acquiring positional data of a contact line between a mandible and a cranium from a sectional image taken from a side vertical plane extending in an axial direction of the cranium and including the contact line;

a calculation means for performing (A) to (D) as follows:

a calculation step (A) wherein rigid body element models, having a unit thickness in a direction perpendicular to the side vertical plane and free from in-plane deformation by stress, are substituted for the mandible and the cranium based on shapes obtained from the positional data of the contact line; regions of the element models along the contact line of the mandible and the cranium are divided into a finite number of plane elements having the unit thickness; vertical springs resisting in a direction vertical to the contact line are assumed for the plane elements in a temporomandibular joint portion among the divided plane elements and a shear spring resisting in a tangential direction and a vertical spring resisting in a direction vertical to the contact line are assumed for the plane elements in a teeth portion; a displacement of the plane elements of the mandible is confined into two dimensional directions within the side vertical plane; stresses produced at the vertical springs in the temporomandibular joint portion, the vertical spring in the teeth portion, and the shear spring in the teeth portion are calculated from the positional data of each of the plane elements using an assumed value of myodynamia as an external force with an assumption that a reaction force from the cranium against the myodynamia is exerted on the mandible in the temporomandibular joint portion and on an arbitrary position in the teeth portion;

a calculation step (B) wherein a determination is made as to whether a negative stress is present at the vertical springs in the temporomandibular joint portion and, if the negative stress is present, a constraint canceling the negative stress is calculated, a force having a same magnitude as and an opposite sign of the constraint is added to the myodynamia, and calculation of the stress in the calculation step (A) is repeated using the corrected myodynamia as the corrected external force;

a calculation step (C) wherein a determination is made as to whether a stress is present at the shear spring in the teeth portion and, if the stress is present, a force canceling the stress is calculated and the calculation of the stress in the calculation step (A) is repeated using corrected myodynamia obtained by adding the canceling force to the myodynamia as the corrected external force; and a calculation step (D) wherein during repetition of the calculation steps (B) and (C), stress at each of the vertical springs in the temporomandibular joint portion is calculated at a moment when the negative stress at the vertical springs in the temporomandibular joint portion and the stress at the shear spring in the teeth portion are both decreased to 0 or a negligible level; and a display means for displaying a distribution of the stress at the vertical springs along the contact line in the temporomandibular joint portion based on a result of the calculations performed by said calculation means.

* * * * *